United States Patent [19]

Seidel

[11] 4,177,215

[45] Dec. 4, 1979

[54] RECOVERY OF TRIARYLBORANES

[75] Inventor: William C. Seidel, Hockessin, Del.

[73] Assignee: E. I. Du Pont de Nemours and Company, Wilmington, Del.

[21] Appl. No.: 925,550

[22] Filed: Jul. 17, 1978

[51] Int. Cl.$^2$ .............................................. C07F 5/02
[52] U.S. Cl. ........................... 260/606.5 B; 260/462 C
[58] Field of Search ...................... 260/606.5 B, 462 C

[56] References Cited

U.S. PATENT DOCUMENTS

| | | | |
|---|---|---|---|
| 2,840,590 | 6/1958 | Muetterties | 260/606.5 B X |
| 2,880,242 | 3/1959 | Hennion | 260/606.5 B |
| 2,880,243 | 3/1959 | Hennion | 260/606.5 B |
| 2,884,441 | 4/1959 | Groszos | 260/606.5 B X |
| 3,030,406 | 4/1962 | Washburn et al. | 260/606.5 B X |
| 3,090,801 | 5/1963 | Washburn et al. | 260/462 C |
| 3,119,857 | 1/1964 | Yates et al. | 260/606.5 B X |
| 3,187,054 | 6/1965 | Willcockson et al. | 260/606.5 B |
| 4,045,495 | 8/1977 | Nazarenko et al. | 260/606.5 B |
| 4,046,815 | 9/1977 | Nazarenko | 260/606.5 B |
| 4,076,756 | 2/1978 | Nazarenko et al. | 260/606.5 B |

Primary Examiner—Helen M. S. Sneed

[57] ABSTRACT

Separating triarylboranes, e.g., triphenylborane from diaryl substituted boranes, e.g., diphenyl borinic acid by precipitation wherein the triaryl borane is present in a basic solution as the adduct while avoiding coprecipitation of the boranes by neutralizing the solution to a pH not less than the pH defined by the equation $$pH = pKn + \log (X)$$

and maintaining the ionic strength of the solution so that it is at least about 1 molar upon completion of the neutralization.

7 Claims, No Drawings

RECOVERY OF TRIARYLBORANES

BACKGROUND OF THE INVENTION

1. Field of the Invention

The present invention is directed to the recovery of triarylboranes and more particularly to the separation of triphenylborane from diphenyl borinic acid by conducting the neutralization to a specified pH in a solution having a specified ionic strength.

2. Description of the Prior Art

Organoboranes have been produced by a variety of methods including the Grignard reaction and more recently by the reaction of an alkali metal, an organohalide and an orthoborate ester. Although the prior art discloses many processes for the preparation of the substituted boron compounds, the prior art does not suggest efficient methods to obtain relatively pure trisubstituted boranes in good yield when significant amounts of other substituted boranes are present.

U.S. Pat. No. 3,090,801 issued on May 21, 1963 to Washburn et al. discloses processes which purport to produce mono, di and trisubstituted boranes in high yields but the patentee's only disclosure of a method for recovery of the boranes is found in the examples. In Example 1 of the patent, the reaction mixture is treated with methanol and water to hydrolize the dimethylboronate to produce the acid form. After the acid form is obtained, the mixture is then distilled to remove xylene, methanol and side reaction products. In Examples 2 and 3, the patentee purports to recover the acid form of the borane by contacting the reaction product with an aqueous solution containing concentrated sulfuric acid followed by extraction or distillation. These recovery procedures are not satisfactory for the trisubstituted boranes because the trisubstituted boranes are relatively unstable and readily degrade in the presence of water and/or acid especially at elevated temperatures.

SUMMARY OF THE INVENTION

The present invention provides a process for separating triarylboranes, e.g., triphenylborane from other substituted boranes having more or less than three aryl substituents and especially the disubstituted boranes, e.g., diphenyl borinic acid wherein the weight ratio of the trisubstituted borane to the disubstituted boranes in the solution is less than about 13:1, i.e., where coprecipitation can occur. These boranes are usually present in a basic solution as their respective salts or adducts.

The triarylborane is recovered as a precipitate by neutralizing the solution to a pH not less than the pH defined by the equation pH=pKn+log (X)

wherein
pKn is the negative log of the product of the dissociation constant and the solubility constant, and
X is the molar concentration of the substituted boranes while maintaining the ionic strength of the solution at at least about 1 molar upon completion of the neutralization. Coprecipitation is thereby avoided and the yield of the triarylborane is maximized. In one preferred embodiment sodium chloride is the ionic source and the boranes are present in a basic solution as their respective sodium salt or adduct while the neutralization is accomplished with dilute hydrochloric acid.

DETAILED DESCRIPTION OF THE INVENTION

The triarylboranes which can be recovered according to the process of the present invention include those of the formula $R_3$-B wherein R is an aryl or substituted aryl group having 6–12 carbon atoms, e.g., phenylorthotolyl, paratolyl, naphthyl, methoxparaphenyl, para-aminophenyl, biphenyl, chlorophenyl and bromophenyl. Separation of triphenylborane from diphenyl borinic acid is of particular interest although the mono and tetrasubstituted boranes wherein the aryl substituent groups are as described above can also be present.

Substantial improvements in the preparation of triaryl substituted boranes are disclosed in U.S. Pat. Nos. 4,046,815; 4,045,495; and 4,076,756, issued on Sept. 6, 1977; Aug. 30, 1977 and Feb. 28, 1977 respectively. These improvements involve reacting an alkali metal, an organohalide, e.g., chlorobenzene and an orthoborate ester, e.g., triisopropylorthoborate in an inert organic solvent such as cyclohexane. The reaction product is contacted with water to form the stable salt or adduct of the trisubstituted borane. Since the salt or adduct is a relatively stable form of the borane, alcohol can be removed by distillation without excessively degrading the borane which can then be recovered in free form by neutralizing the salt or adduct to a pH not less than about 6.0. These disclosures teach that the ratio of triaryl substituted borane, e.g., triphenylborane to the disubstituted borane, e.g., diphenyl borinic acid should be maintained at greater than 13:1 and preferably greater than 15:1 to insure a satisfactory yield of triarylborane upon neutralization. Coprecipitation of the disubstituted borinic acid with trisubstituted boranes is not significant at these high ratios because the disubstituted borinic acid remains in solution and the autocatalytic degradation of the trisubstituted boranes by that acid does not occur to any significant degree. Neutralization of solutions wherein the aforementioned ratios are less than 13:1 to maximize recovery of the trisubstituted borane results in coprecipitation of the borinic acid and concomitant degradation of the trisubstituted product. It is suggested in the above discussed disclosures that the coprecipitation can be avoided by diluting the salt solution with water to avoid precipitation of the disubstituted borane, however, the handling of this additional water increases the complexity and the cost of recovery.

The process of the present invention is applied to the recovery of products produced by the improved processes above described wherein coprecipitation is likely to occur, i.e., the ratio of trisubstituted to disubstituted boranes as salts or adducts in aqueous solution is less than 13:1. Triaryl-substituted borane of satisfactory purity cannot be obtained without loss of significant amounts of the desired product when recovery is attempted according to known techniques. In one embodiment, the solutions containing the adducts of triarylboranes are prepared by reacting a finely divided alkali metal such as lithium, potassium, etc., and preferably sodium with an organo-halide such as an aryl halide, e.g., chlorobenzene, and an orthoborate ester derived from secondary alkyl alcohol, e.g., isopropanol and sec-butanol in an inert organic solvent at a temperature in the range 15°–120° C.

The organohalide can be any halogen substituted organic and is preferably an aryl or a substituted aryl halide wherein the aryl group has 6–10 carbon atoms. Examples of suitable compounds include chlorobenzene, bromobenzene, chlorotoluene, chloroaniline and the like.

The orthoborate esters which are suitable for reaction include those derived from an alcohol containing 1–10 carbon atoms which is represented by the formula $B(OR)_3$ wherein R is a alkyl group such as methyl, ethyl, isopropyl etc. wherein the R's may be same or different. Preferred esters are those derived from secondary alcohols having 3–10 carbon atoms when used in conjunction with a cyclohexane solvent. Suitable solvents are those which are substantially inert with respect to the reactants and preferably exhibit a boiling point near atmospheric pressure to facilitate heat removal from the reaction mixture. Examples of suitable solvents singly or in combination are branched or unbranched hydrocarbons having 5–10 carbon atoms, e.g., alkanes such as pentane, hexane, octane and 3-methyl pentane; cyclohexane, cyclooctane, cyclopentane; alkenes and cycloalkenes wherein the unsaturation does not react with the alkali metal, the organohalide or the orthoester. Such unsaturated solvents include hexene and octene. Useful aromatic hydrocarbons include xylene, benzene and the like.

After the reaction is complete, the reaction mixture is contacted with water, whereupon the alkali metal hydroxide salt, i.e., adduct of the triarylborane is formed along with the salts of the under or over phenylated boron compounds, e.g., diphenyl borinic acid. Since the salts are stable in the aforementioned solution, volatile compounds which interfere with recovery of the trisubstituted boranes can be removed without excessive degradation of the borane. A suitable method for removal of such compounds, e.g., alcohol, is distillation. After removal of the volatile compounds, the solution is neutralized.

Under optimum conditions, the ratio of the trisubstituted boranes to the disubstituted boranes will be greater than 20:1 and thus the above mentioned neutralization produces a triarylborane of satisfactory purity and minimum contamination of products which tend to degrade the borane. However, if the process is operated under less than optimum conditions, the ratio of trisubstituted boranes to disubstituted boranes can decrease to less than about 13:1. It is under these nonoptimum conditions that the present process is particularly advantageous since neutralization to a degree necessary for high yield will result in a trisubstituted product which has a high percentage of disubstituted borane therein. Diaryl borinic acids are potent catalysts for the hydrolytic degradation of triarylboranes especially triphenylborane which is degraded to diphenyl borinic acid and benzene. This degradation therefore is autocatalytic and causes the triarylborane to readily decompose. The present invention provides a method for recovering triarylboranes of satisfactory purity from such solutions at maximum yields by conducting the neutralization to a pH not lower than a certain value while maintaining a specified ionic concentration in the solution. Such separation is possible because it has been discovered that the trisubstituted boranes will precipitate from an aqueous solution at a higher pH than the disubstituted products. Thus, if the neutralization is conducted to a pH above the pH where the disubstituted boranes precipitate, a relatively pure trisubstituted borane can be recovered.

The lowest pH for this end point of the neutralization can be expressed by the equation $$pH = pKn + \log (X)$$

wherein pKn is the negative log of the product of the dissociation constant and the solubility constant of borinic acid and X is the molar concentration of the borinic acid salt. Thus, if one adheres to the aforementioned formula, i.e., does not reduce the pH of the system beyond that wherein substantial amounts of disubstituted boranes begin to precipitate along with the trisubstituted boranes one can obtain a relatively pure trisubstituted product. Although increasing the pH at the end point of the neutralization minimizes the tendency for the borinic acid to precipitate, it also increases the loss of the trisubstituted product. It has been discovered that this loss can be minimized without sacrificing purity of the trisubstituted borane by increasing the ionic strength of the system. This is possible because the responses to increase in the ionic strength (as measured by pKn) surprisingly differ for the di and trisubstituted boranes. As the ionic strength of the system is increased above about 1 molar the pH at which the trisubstituted borane begins to precipitate increases more rapidly than that of the disubstituted borane and more desired product of acceptable purity can be obtained. The ionic strength of the system is reflected in the term pKn.

The pKn is readily determined for a given system by measurements known to those skilled in the art. As a specific example for the aqueous system where the ionic strength is provided by sodium chloride, the boranes present as salts or adducts are the desired triphenyl borane adduct and the salt of diphenyl borinic acid as the undesirable impurity the pKn for diphenyl borinic acid is determined by dissolving various amounts of the acid in an aqueous sodium hydroxide solution, adding various amounts of sodium chloride, reducing the pH with dilute hydrochloric acid and noting the pH where the diphenyl borinic acid begins to precipitate for each concentration and ionic strength. Using the information generated as above the pKn is calculated from the equation $$pH = pKn + \log [\phi_2 BO^-]$$

and plotted against the ionic strength. The equation for the curve defined by the above points is fitted to the general formula for the function $$pKn = A(I)^2 + B(I) + C$$

The constants for the above described system are then determined to yield the equation $$pKn = 0.037(I)^2 + 0.048(I) + 8.75$$

wherein I is the ionic concentration. The minimum pH to which the system can be reduced to yield triphenylborane of acceptable purity is determined by substituting the above expression for pKn in the equation $$pH = pKn + \log (X)$$

wherein X is the molar concentration of the salt of borinic acid.

Although the above discussion is directed principally to triphenylboron and diphenyl borinic acid with the ionic concentration being adjusted with sodium chloride, it is understood that this relationship applies to other trisubstituted boranes and other ionic sources as set forth herein.

The source and method of introduction of the ions is not critical to the present invention. Alkali and alkaline earth metal halides, e.g., sodium chloride, lithium iodide, potassium bromide and calcium chloride, sulfates, e.g., sodium sulfate, carbonates, e.g., sodium carbonate and organic salts of the aforementioned metals, e.g., sodium acetate and citrate can be employed. Examples of other suitable ion sources include nitrates, e.g., sodium nitrate and calcium nitrate, transition metal salts, e.g., ferric bromide and cobalt chloride and copper and zinc chloride. In general, any salt which is sufficiently ionizable in the medium and which does not react with or degrade the triphenylboron can be employed. The salts may be introduced at any time before the final pH is reached but preferably added during the preparation of the adduct solution or to a solution of the adduct before neutralization.

Preferably the ionic strength is maintained in the range of about 1–4 molar. In some cases it is preferred to maintain the ionic concentration so that it is at least 1.5 molar. In one preferred embodiment the source of the ions is sodium chloride obtained from the neutralization of the excess base employed in forming the adduct. As should be obvious to one skilled in the art the maximum amount of salt employed is dictated in large part by its solubility in the system.

The following examples are presented to illustrate but not to restrict the present invention. Parts and percentages are by weight unless otherwise specified.

EXAMPLE 1

The apparatus employed to produce the aqueous solution of the hydroxide adduct of triphenylborane consisted of a 500 ml four-necked flask equipped with a mechanical stirrer, thermometer, addition funnel and relux condenser with suitable provisions to maintain a nitrogen atmosphere over the reactants. Approximately 6.0 g of finely divided sodium were mixed with 50 ml of cyclohexane and charged to the above-described reaction flask, following which a mixture of 12.6 g of chlorobenzene and 7.6 g of isopropylorthoborate in the 60 ml of cyclohexane were introduced over a 2 hr period while maintaining the reaction at 80° C. After addition of the chlorobenzene and isopropylorthoborate, the contents of the flask were permitted to cool slowly to room temperature following which 60 ml of water were introduced into the flask. The resultant aqueous and organic phases were removed from the flask and separated. The aqueous phase (100 g) contained 8.23% triphenylborane and 1.64% borinic acid by analysis (ratio 5/1). Isopropanol was flashed distilled as the water azeotrope from the aforementioned aqueous solution and water was added to the tails to return the aqueous phase to its original volume. This resultant aqueous phase was divided into two equal 47 g portions and titrated as follows. Using the known ionic concentration (2.6 mols/l) of the aqueous phase and the concentration of the diphenylborane anion (0.1 mols/l), it was determined by equation that the minimum pH to which the system could be titrated as 8.1 and accordingly one portion of the aqueous phase was titrated to pH 8.3 using three normal hydrochloric acid. The resultant slurry was then filtered and the recovered white solid contained 3.42 g of triphenylborane (representing an 88.4% yield from the sodium hydroxide adduct) and 0.14 g of diphenyl borinic acid (ratio 24/1). It may be seen from the foregoing experiment that by adhering to the minimum pH defined by the equation set forth hereinabove that the ratio of triphenylborane to borinic acid was improved from 5:1 which was a product exhibiting unsatisfactory characteristics to 24:1 which is a product exhibiting satisfactory characteristics.

COMPARATIVE

As a comparison, the second portion of the above-described aqueous solution was titrated to a pH of 7.18 with 3 normal hydrochloric acid which is the pH for the maximum recovery of triphenylborane when its ratio to diphenylborinic acid is greater than 13/1. The precipitate was isolated and this white solid contained 3.05 of triphenylborane (78.8% yield from the sodium hydroxide adduct) and 1.39 g of diphenylborinic acid (ratio 2.2/1). It may seem that from this comparison that failure to adhere to the minimum pH resulted in coprecipitation of the tri and disubstituted materials with recovery of a product that was poorer in quality than the starting material. This comparison further demonstrates that the precipitation of excessive amounts of borinic acid along with the triphenylborane results in increased degradation, i.e., a lower yield of the desired trisubstituted product.

EXAMPLES 2–4

Triphenylborane, isopropyl diphenylborinate and sodium hydroxide were combined with water to provide a solution containing 0.0718 g/ml triphenylborane as the sodium hydroxide adduct, 0.015 g/ml of borinic acid as the sodium salt (0.05 moles/l of boronate ion) and 0.8 mols/l sodium ion. The ratio of trisubstituted to disubstituted boranes in this solution was 5:1. Salts of varying ionic charges were added to 48.0 ml portions of this solution so as to provide a final molar ionic strength after neutralization of 2.7. Using these values in the equation set forth above, the minimum pH was determined to be 7.9. Each of the solutions were titrated to a pH of 8.1 using 1.074 normal HCl. The resultant slurries were filtered, the cakes washed with water, dried and analyzed, the results are reported in Table 1. Essentially no triphenylborane was detected in the filtrate.

EXAMPLE 5

To approximately 50 ml of a caustic solution containing 0.981 g/ml of triphenylborane (as the adduct), and 0.018 g/ml of diphenylborinic acid salt (triphenylborane:borinic acid ratio of 5) was added 8.3 g of sodium citrate, to give a final ionic strength of 2.5 molar. The calculated minimum pH was 8.18. The sample was titrated with dilute hydrochloric acid to a pH of 8.1. The results are reported in Table I. Essentially no triphenylborane was detected in the filtrate.

Table I

| Example No | Salt Added | Wt (g) | % Yield to $\phi_3B$ | $\phi_3B/\phi_2BOH$ (Solid) |
|---|---|---|---|---|
| 2 | NaCl | 10.2 | 98.8 | 24 |
| 3 | CaCl$_2$ | 6.4 | 97.1 | 58 |
| 4 | Na$_2$SO$_4$ | 8.3 | 98.1 | 23 |
| 5 | Na$_3$C$_6$H$_5$O$_7$ . 2H$_2$O | 8.3 | 97.1 | 25 |

EXAMPLE 6

An aqueous solution was prepared by combining 4.8 g of triphenylborane, 0.7 ml of isopropyl diphenyl boronate, 2.8 g sodium chloride, 1.2 g sodium hydroxide and approximately 50 ml of water (weight ratio of $\phi_3B/\phi_2BOH$ of 7.9). Using 1.074 N hydrochloric acid to neutralize the solution, the final ionic strength was determined to be 1 molar and the borinate anion concentration to be 0.043 molar. The minimum calculated pH was 7.5. The solution was titrated to a pH of 7.6 with 25.8 ml of the dilute hydrochloric acid. A white solid containing 4.29 g of triphenylborane (96.1% yield from the adduct) and 0.152 g of borinic was recovered (ratio $\phi_3B/\phi_2BOH=28$. Only trace amounts of triphenylborane were detected in the filtrate.

I claim:

1. A process for separating triarylboranes from other aryl substituted boranes wherein the boranes are present in a basic solution and wherein the weight ratio of the trisubstituted boranes to the other substituted boranes in the solution is sufficiently low so that coprecipitation of the boranes can occur which process comprises neutralizing said solution to a pH not less than the pH defined by the equation $$pH = pKn + \log (X)$$

wherein pKn is negative log of the product of the dissociation constant and the solubility constant, and X is the molar concentration of the substituted boranes other than the triaryl substituted borane while maintaining the ionic strength of the solution at at least about 1 molar upon completion of the neutralization.

2. The process of claim 1 wherein the ionic strength is at least 1.5 molar.

3. The process of claim 2 wherein the ionic strength of the solution is obtained at least in part from a soluble salt selected from the class consisting of alkali and alkaline earth salts and mixtures thereof.

4. The process of claim 3 wherein the salt is sodium chloride and hydrochloric acid is employed to effect the neutralization.

5. The process for separating triphenylborane from diphenyl borinic acid wherein the boranes are present in a basic aqueous solution and wherein the weight ratio of triphenylborane to borinic acid is less than about 13:1 which process comprises neutralizing the solution to a pH not less than the pH defined by the equation $$pH = 0.037(I)^2 + 0.048(I) + 8.75 + \log (\phi_2BO^-)$$

wherein

I is the ionic strength of the solution which is maintained at no less than about 1 molar, and $(\phi_2BO^-)$ is the concentration of the salt of diphenyl borinic acid in moles per liter of solution.

6. The process of claim 5 wherein the ionic strength of the solution is maintained at no less than 1.5.

7. The process of claim 4 wherein the triphenylborane is present as the sodium adduct, the borinic acid is present as the sodium salt and the neutralization is effected with hydrochloric acid.

* * * * *